United States Patent
Roncone et al.

(10) Patent No.: US 6,952,256 B2
(45) Date of Patent: Oct. 4, 2005

(54) OPTICAL COMPENSATION IN HIGH NUMERICAL APERTURE PHOTOMASK INSPECTION SYSTEMS FOR INSPECTING PHOTOMASKS THROUGH THICK PELLICLES

(75) Inventors: Ronald L. Roncone, Sunnyvale, CA (US); Damon Kvamme, Los Gatos, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 106 days.

(21) Appl. No.: 10/401,614

(22) Filed: Mar. 27, 2003

(65) Prior Publication Data

US 2004/0042002 A1 Mar. 4, 2004

Related U.S. Application Data

(60) Provisional application No. 60/407,593, filed on Aug. 30, 2002.

(51) Int. Cl.[7] .............................................. G01N 21/88
(52) U.S. Cl. ............................... 356/237.2; 356/239.2; 359/691
(58) Field of Search ......................... 356/237.2–237.5, 356/239.1, 239.2, 239.7, 239.8; 359/691

(56) References Cited

U.S. PATENT DOCUMENTS

| | | | |
|---|---|---|---|
| 4,303,324 A | 12/1981 | Marcus ...................... 354/195 |
| 4,426,137 A | 1/1984 | Mori .......................... 350/471 |
| 4,781,445 A | 11/1988 | Baba et al. ................. 350/409 |

(Continued)

OTHER PUBLICATIONS

International Search Report, dated Jan. 25, 2005.

Primary Examiner—Richard A. Rosenberger
(74) Attorney, Agent, or Firm—Beyer Weaver & Thomas LLP

(57) ABSTRACT

An objective lens system having reconfigurable optical components that enable the inspection of inspection surfaces in the absence of a pellicle or through a thin membrane pellicle, and using the same system, also enabling the inspection of inspection surfaces through a thick pellicle. An objective lens system includes a first group and a second group of optical elements. The first group of optical elements enables high numerical aperture and beam contraction. The second group of optical elements is capable of two mode operation enabling, in one mode, inspection through a thin membrane pellicle or in the absence of a pellicle and in another mode, enabling inspection through a thick pellicle. The system can also be enhanced through the use of an interposable aberration corrector plate that is used to correct optical aberrations caused by the presence, absence, or thickness of pellicles.

29 Claims, 6 Drawing Sheets

U.S. PATENT DOCUMENTS

| | | | |
|---|---|---|---|
| 4,783,155 A | 11/1988 | Imataki et al. | 350/423 |
| 5,018,854 A | 5/1991 | Rioux | 356/376 |
| 5,075,561 A | 12/1991 | Rioux | 250/561 |
| RE33,956 E * | 6/1992 | Lin et al. | 250/550 |
| 5,455,677 A | 10/1995 | Yoshizumi et al. | 356/376 |
| 5,548,449 A | 8/1996 | Matsui et al. | 359/814 |
| 5,602,639 A | 2/1997 | Kohno | 356/237 |
| 5,739,958 A * | 4/1998 | Abe | 359/660 |
| 5,757,469 A | 5/1998 | Allen | 355/53 |
| 5,946,100 A | 8/1999 | Ishihara | 356/376 |
| 5,963,316 A | 10/1999 | Miura et al. | 356/237.3 |
| 5,982,564 A | 11/1999 | Nagai | 359/814 |
| 6,038,080 A | 3/2000 | Schachar | 359/666 |
| 6,064,477 A * | 5/2000 | Matsumoto et al. | 356/237.2 |
| 6,069,690 A | 5/2000 | Xu et al. | 356/73 |
| 6,084,664 A | 7/2000 | Matsumoto et al. | 356/237.4 |
| 6,108,090 A | 8/2000 | Ishihara | 356/376 |
| 6,122,048 A | 9/2000 | Cochran et al. | 356/239.4 |
| 6,137,580 A | 10/2000 | Gelbart | 356/401 |
| 6,188,530 B1 | 2/2001 | Katsuragi | 359/824 |
| 6,198,529 B1 | 3/2001 | Clark, Jr. et al. | 356/237.5 |
| 6,215,605 B1 | 4/2001 | Kuwana et al. | 359/824 |
| 6,313,467 B1 | 11/2001 | Shafer et al. | 250/372 |
| 6,369,888 B1 | 4/2002 | Karpol et al. | 356/237.5 |
| 6,369,963 B1 | 4/2002 | Hotta et al. | 359/824 |
| 6,373,978 B1 | 4/2002 | Ishihara | 382/154 |
| 6,392,793 B1 | 5/2002 | Chuang et al. | 359/364 |
| 6,392,827 B1 | 5/2002 | Ueyama et al. | 359/824 |
| 2001/0019625 A1 | 9/2001 | Kenan et al. | 382/144 |
| 2002/0048096 A1 | 4/2002 | Melzer et al. | 359/846 |
| 2002/0060863 A1 | 5/2002 | Ohtaka | 359/824 |

* cited by examiner

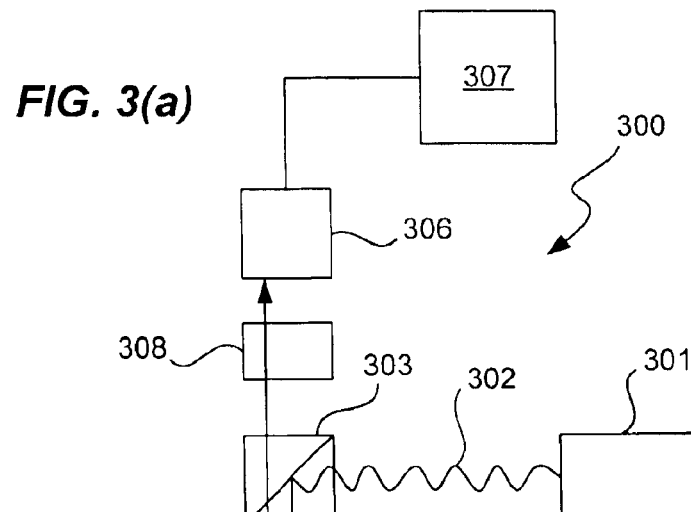
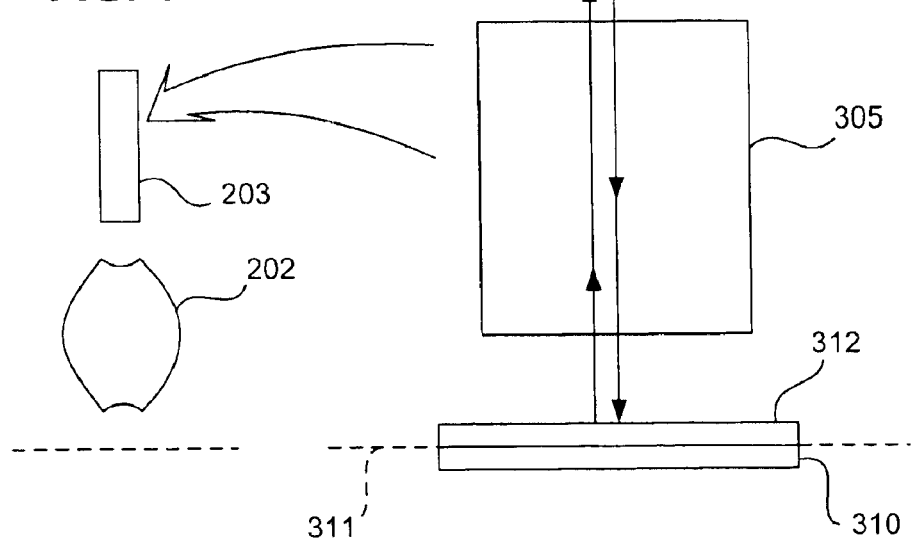

OPTICAL COMPENSATION IN HIGH NUMERICAL APERTURE PHOTOMASK INSPECTION SYSTEMS FOR INSPECTING PHOTOMASKS THROUGH THICK PELLICLES

RELATED APPLICATION

This application claims priority, under 35 U.S.C. 119(e), to the U.S. provisional application entitled "Optical Compensation in High Numerical Aperture Reticle Inspection Systems for Inspecting Surfaces with Thick Pellicles", filed Aug. 30, 2002, by inventors Ronald L. Roncone and Damon Kvamme, U.S. Provisional Application No. 60/407,593, which is incorporated by reference.

TECHNICAL FIELD

The invention described herein relates generally to surface inspection semiconductor photomask inspection. In particular, the invention relates to an objective lens system capable of inspecting photomasks through thick pellicles, thin pellicles, or in the absence of a pellicle.

BACKGROUND OF THE INVENTION

In semiconductor processing, photomasks are used in photolithographic processes to define circuit structures on semiconductor substrates. Such masks are protected from environmental contamination and other effects by thin membrane pellicles. Commonly, such pellicles are formed of very thin membranes of organic material. Typically, such thin pellicles are on the order of less than about two micron ($\mu$m) thick. With the ever increasing drive toward smaller features sizes and increasing circuit densities, the industry is driven toward the need to obtain higher resolution in the transfer of mask patterns onto semiconductor substrates. One means of achieving this increased resolution is through the use of shorter wavelength exposure sources. One exposure source coming into ever increasing use is the deep ultraviolet (DUV) laser. Typical examples of such lasers are ArF (argon fluoride) lasers and $F_2$ (fluorine) lasers. In common implementation, the $F_2$ laser generates an exposing light beam having a wavelength of 157 nm (nanometers).

Such short wavelength exposure sources can damage conventional thin membrane pellicles after only a few exposures to 157 nm light at typical exposure levels. As reliance on 157 nm exposure sources increases, the traditional thin membrane organic pellicles currently used to protect the mask surface can no longer be used. Consequently, the industry is developing thick fused silica pellicles as an alternative. As used herein, "thick pellicles" are defined as pellicles thicker than about 2 $\mu$m thick (particularly, 300 $\mu$m and 800 $\mu$m thick pellicles). Industry organizations such as SEMATECH and its Japanese analog SELETE have called for the use of 800 $\mu$m fused silica pellicles having a thickness tolerance of about ±0.5 $\mu$m. Although these thick pellicles are more rugged in the face of UV exposure, the use of these new thicker pellicles presents significant optical problems for the conventional optical systems used in current photomask inspection tools.

In conventional optical systems and inspection tools, the thin organic pellicles are so thin as to be optically insignificant to the optical system, and, in general, can be ignored. For example, in inspection systems having numerical apertures (NA) of 0.8 or less, pellicle thicknesses of 2 $\mu$m or thinner have negligible effect on system optical performance, and can be ignored.

In contrast, the thick pellicles proposed by SELETE and SEMATECH will induce significant optical effects that must be corrected in order to obtain satisfactory resolution.

To resolve very small features on a photomask requires a very high resolution imaging system. The resolution of an optical system can be represented by $2*NA/\lambda$, where NA is numerical aperture, and $\lambda$ is the wavelength of light. Thus, to increase resolution (i.e. to see smaller defects), NA can be increased, $\lambda$ can be decreased, or both may occur. For high-resolution photomask inspection stations, NA can be pushed beyond 0.8, and $\lambda$ can be decreased into the UV and DUV regions of the spectrum. However, to detect the smallest of defects under these conditions, these imaging systems must have P-V wavefront errors of well under $\lambda/4$ (the well-known Raleigh Criteria) where $\lambda$ is the wavelength of light used to image the defects. Therefore, the highly aberrated wavefront that results from passing a beam of light through an 800 $\mu$m thick pellicle at high NA values, must be corrected. Without such correction, the image quality would be so poor that even large, high contrast defects would be missed during inspection. Thus, it is important that the industry find a solution to this very serious problem.

FIGS. 1(a)–1(c) present a simplified illustration of one aspect of the problems introduced by using thick pellicles. FIG. 1(a) is a simplified and schematic depiction of a generic conventional objective lens system 101. A light beam 102 is passed through the objective lens system 101 where it becomes focused at a point 103 in the image plane 104 of the objective lens system 101. Commonly, many optical elements are used by the objective lens system 101 to correct for a variety of optical aberrations to accomplish the needs of the objective lens system 101. Such optical elements commonly include lenses, lens groups, gratings, apertures, filters, as well as a number of other optical devices known to those having ordinary skill in the art. In a surface inspection tool, an object 105 (e.g., a photomask) being inspected is positioned at the image plane 104 for inspection by the tool.

FIG. 1(b) depicts the same objective lens system 101 as shown in FIG. 1(a). A conventional thin membrane pellicle 106 (e.g., pellicles having a thickness of 2 $\mu$m or less) is interposed between the objective lens system 101 and the object 105. As is depicted, the light beam 102 is passed through the objective lens system 101 and is focused at point 103 in the image plane 104. The presence of the thin pellicle 106 has a negligible effect on the light beam. As a result, until now there has not been a need to address the optical effects induced by the presence (or absence) of pellicles.

FIG. 1(c) is a simplified and schematic illustration depicting some of the problems induced by the interposition of a thick pellicle 107 between a conventional objective lens system 101 and an inspection surface (not shown in this view). The light beam 102 passes through the objective lens system 101 onto the thick pellicle 107. The thick pellicle 107 functions as an aberration inducing optical element. An aberration so produced can be generally described as an aperture dependent focus, which results from a beam 102 passing through the thick pellicle 107. This is illustrated in FIG. 1(c) using a few example aperture locations and resultant focal points (110, 111, 112). The presence of the thick pellicle aberrates the light beam 102 such that there is no single focal plane where the parts of the incident beam entering different parts of the aperture, are all in focus. The end result is a blurry, low contrast image. Such a distorted light beam cannot be used to effectively image small defects on a photomask surface. Thus, solutions to this problem are needed.

In particular, there is a need for a lens system (and accompanying inspection tool) capable of inspecting objects through both thick and thin pellicles (or in the absence of pellicles). In some embodiments, the system should also be capable of obtaining a high numerical aperture (NA) and a relatively long working distance. Moreover, it is especially advantageous for such a system to achieve such inspection flexibility by changing, moving, adding or removing only a few optical elements.

SUMMARY OF THE INVENTION

The principles of the invention involve an objective lens system having reconfigurable optical components that enable the inspection of objects in the absence of a pellicle or through a thin membrane pellicle, and using the same lens system, also enable the inspection of objects through a thick pellicle.

Embodiments of the invention include an objective lens system having a first group and a second group of optical elements. The first group of optical elements enables high numerical aperture and beam contraction for light passing through the first group of optical elements. The second group of optical elements, when switched to a first mode of operation, enables the lens system to inspect a target surface through a thin membrane pellicle or in the absence of a pellicle. When the second group of optical elements is switched to a second mode of operation it enables the lens system to inspect the target surface through a thick pellicle.

In another embodiment an optical inspection tool is disclosed. The inspection tool comprises a light source, an optical system, a detection system, and an image processor. The optical system includes an objective lens system. The objective lens system is configured for achieving a high numerical aperture, a long working distance, and configured such that in one mode of operation an inspection surface can be inspected through a thin pellicle or in the absence of a pellicle. In another mode of operation, the inspection surface can be inspected through a thick pellicle. In a related embodiment, a corrector plate can be used in the objective lens system to further enhance the optical properties of the inspection tool.

These and other aspects of the present invention are described in greater detail in the detailed description of the drawings set forth herein below.

BRIEF DESCRIPTION OF THE DRAWINGS

The following detailed description will be more readily understood in conjunction with the accompanying drawings, in which:

FIGS. 3(a) and 3(b) are simplified schematic depictions of optical inspection tool embodiments constructed in accordance with the principles of the invention.

FIG. 4 is a simplified schematic depiction of an objective lens system embodiment used with an optical inspection tool constructed in accordance with the principles of the invention.

It is to be understood that, in the drawings, like reference numerals designate like structural elements. Also, it is understood that the depictions in the Figures are not necessarily to scale.

DETAILED DESCRIPTION OF THE INVENTION

Figure 1A:
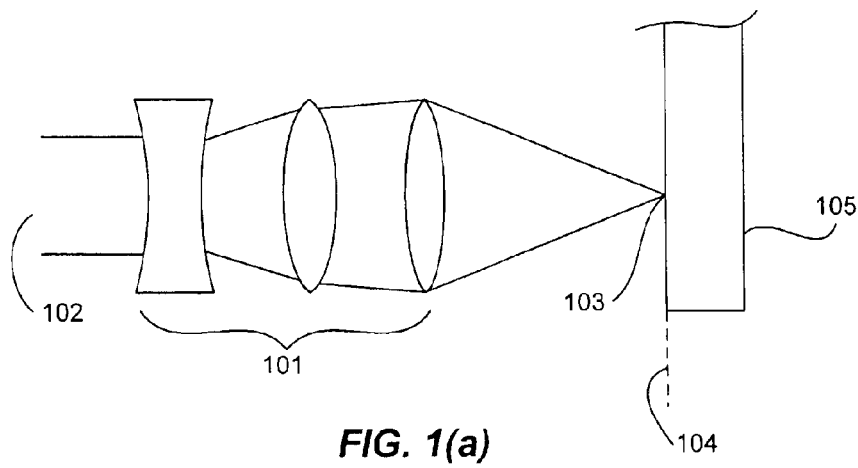
FIGS. 1(a)–1(c) schematically depict simplified conventional objective lenses and the effect on a light beam when no pellicle, a thin pellicle, and a thick pellicle are used.
Figure 1B:
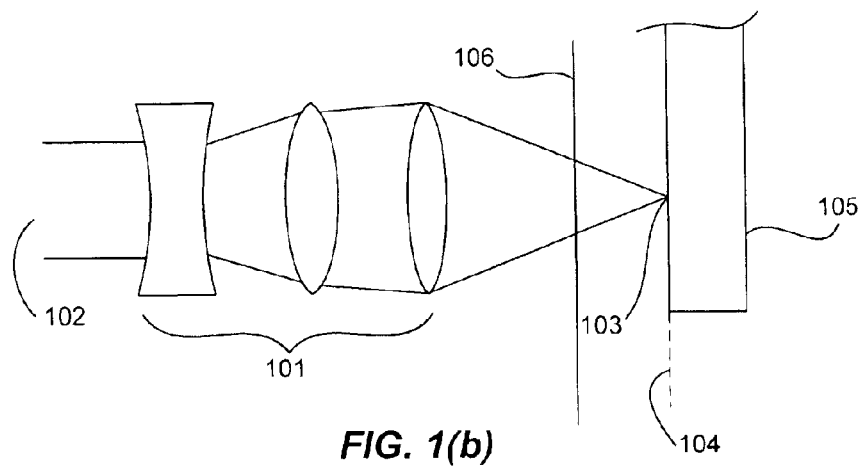
Figure 1C:
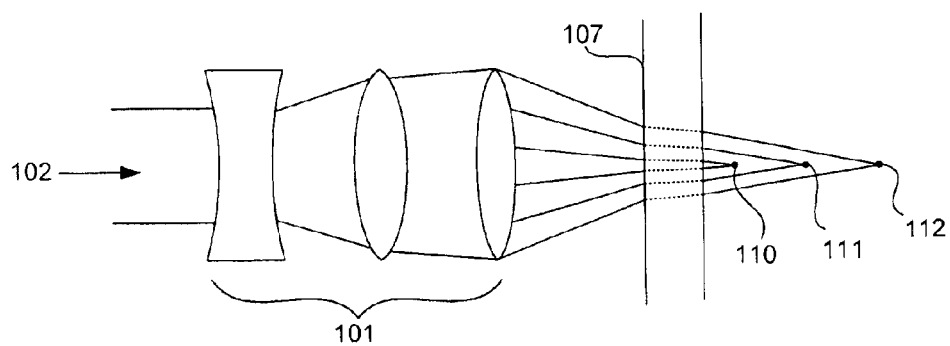

The present invention has been particularly shown and described with respect to certain embodiments and specific features thereof. The embodiments set forth hereinbelow are to be taken as illustrative rather than limiting. It should be readily apparent to those of ordinary skill in the art that various changes and modifications in form and detail may be made without departing from the spirit and scope of the invention.

From a practical standpoint it is desirable that inspection stations used to inspect photomasks for use in 157 nm lithography, will also have to be able to inspect pellicles for use at 193 nm, 248 nm, and 365 nm lithography. Thus, inspection stations that support 157 nm lithography (i.e. thick pellicles) should also support lithography at other wavelengths (i.e thin membrane pellicles or no pellicles). Thus, it is desirable to have an objective lens system that can support inspection through both thick and thin pellicles. In principle, one could conceive of designing two completely different objective lenses, one for imaging through thick pellicles, and one for imaging through thin/no pellicles, and somehow switch these in the inspection station, depending on the type of pellicle (and thus, photomask) in use. However, this would be an extremely daunting task, from both financial and technical perspectives. For example, achieving switching of two objective lenses and their mounts (weighing in excess of 20 pounds) into position, while retaining alignment tolerances on the micron scale, is extremely difficult. Additionally, such large lens systems occupy large amounts of critical space in an inspection machine. Also, from a cost standpoint such complete changing of lens systems is a very expensive proposition. Objective lens systems used in the current art are extremely expensive optical components. It is common for these multi-lens optical structures to cost in excess of $75,000.

One cost effective approach to dealing with the challenges presented by the introduction of thick pellicles is to create a lens system having a combination of constant (unchanging) optical components and reconfigurable (e.g., switchable, movable, changeable, or interchangeable) optical components. In such a system, a portion of the lens system remains constant regardless of the type of pellicle used. Additionally, the reconfigurable portion of the lens system is altered to accommodate the optical requirements of the type of pellicle used. For example, in one mode of operation the reconfigurable portion of the lens system is set at a first setting that optimizes the lens system for use when a thin pellicle is used or when no pellicle at all is used. In a second mode of operation, the reconfigurable portion of the lens system is switched to a second setting such that the overall lens system is optimized for use with a thick pellicle.

The forgoing approach is extremely attractive because it means that only a portion of the lenses of the objective lens system need be changed (or moved or otherwise reconfigured) at any one time in order to image a photomask (or other desired object) through thick, thin, or no pellicles.

By only changing a few of the lenses instead of the entire lens system, the costs related to such systems are significantly reduced.

Figure 2A:
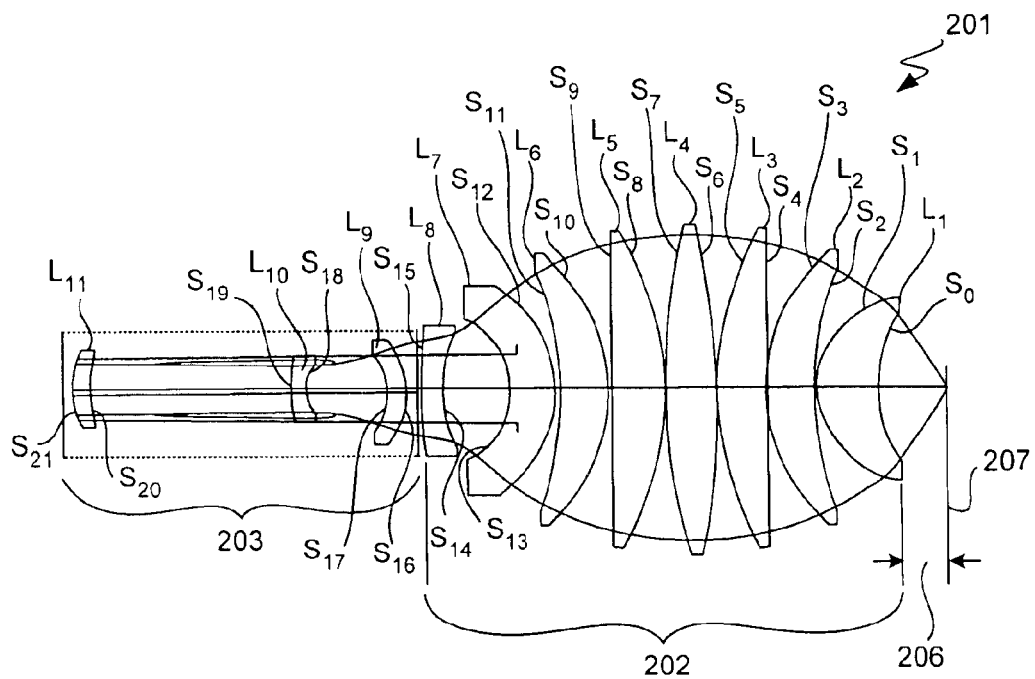
FIGS. 2(a) and 2(b) are simplified schematic depictions of an objective lens system constructed in accordance with the principles of the invention.
Figure 2B:
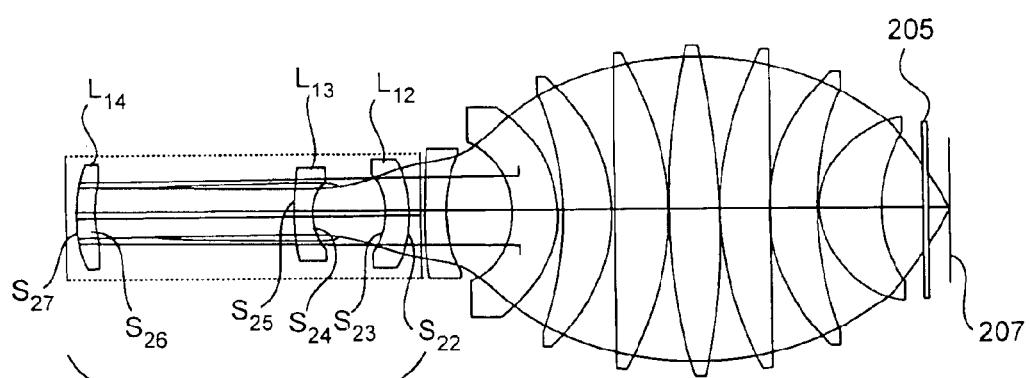

FIGS. 2(a) and 2(b) schematically depict two example modes of operation of one such objective lens system embodiment. FIG. 2(a) depicts an objective lens system 201 having a first group of optical elements 202 at the finite conjugate side of the objective lens system 201 and a second group of optical elements 203 on the infinite conjugate side of the objective lens 201. The first group of optical elements 202 is configured to achieve a high numerical aperture, generate a relatively long working distance, reduce aberration, and achieve beam contraction for light passing through the first group of optical elements 202.

In the context of this patent, a high numerical aperture (NA) for the objective lens system comprises an NA greater than about 0.65 and preferably greater than about 0.85. As is known to persons of ordinary skill in the art, the numerical aperture (NA) is the sine of the half angle of the image-forming cone of light as modified by the medium the light is traveling in (i.e., NA=n sin θ where n is the refractive index of the medium in which the light is traveling and where θ is half the angle of the image-forming cone of light).

Additionally, in the context of this patent a long working distance for the objective lens system is greater than about 6.5 mm and preferably greater than about 8 mm. The working distance is defined as the distance 206 between the front face of the last optical element (here, $L_1$) of the lens system 201 and the image plane 207 of the lens system 201. Typically, the pellicle has a standoff distance of 6.5 mm from the photomask. Thus, a working distance greater than 6.5 mm is typically used to prevent the objective lens from interfering with or crashing into the pellicle. Beam contraction refers to the beam converging properties of the first group of optical elements 202 as a light beam passes through the finite conjugate side of the objective lens system 201.

With continued reference to FIGS. 2(a) and 2(b), the depicted objective lens system 201 also includes a second group of optical elements 203 (positioned at the infinite conjugate side of the objective lens 201). The second group of optical elements 203 is a reconfigurable group of optical elements that functions as an optical aberration compensator. In the depicted embodiment, the second group of optical elements 203 has two modes of operation. FIG. 2(a) depicts the second group of optical elements 203 configured in a first mode of operation. In the first mode, the second group of optical elements 203 enables the lens system 201 to inspect an inspection surface through a thin membrane pellicle or in the absence of a pellicle.

As depicted in FIG. 2(b), the second group of optical elements can be switched to a second mode of operation 203' that enables the lens system 201 to inspect an inspection surface through a thick pellicle. This second mode of operation 203' is described in greater detail elsewhere in this patent.

The basic idea of such optical systems is that some number of elements (e.g., the second group of optical elements 203) can be changed (or in some implementations elements can be moved or additional elements can be introduced or elements removed) depending upon whether imaging is to be conducted through the thick or thin pellicles. Advantageously, other optical system specifications (EFL (Effective Focal Length), magnification, system length, pupil plane position, working distance, etc.) can remain the same for both modes of operation.

The elegance of this design is that the entire finite conjugate side of the objective (e.g., the first group of optical elements 202 defining 7, 8, 9 or possibly more elements) remains exactly the same regardless of whether the photomask (or other object) is imaged through either thick or thin pellicles (or no pellicle). These optical elements generally comprise the larger, more difficult to fabricate lenses, with tighter optical and mechanical mounting tolerances. Thus, by changing only two or three small elements (or in some cases even one element) in the second group of optical elements 203, this embodiment can be used to image through both thin and thick pellicles. Moreover, these elements 203 (and 203') are generally the least expensive and easiest to manufacture components of the system 201.

Thus, if imaging is to be conducted through thick and thin pellicles using the same inspection machine, two different sets of optics (203, 203') can be shuttled into place on the back end of the objective lens system 201, dependent upon whether thick or thin pellicles are used. Consequently, this scheme provides for a reconfigurable high NA DUV objective lens 201 that can be easily modified to support inspection of photomasks with either thin or thick pellicles on the same inspection platform, using a single objective lens system 201, with a reconfigurable back end (e.g., the second group of optical elements 203, 203').

With continued reference to FIGS. 2(a) and 2(b), a typical objective lens system of this type is depicted. FIG. 2(a) depicts an embodiment of an objective lens system 201 configured to inspect an inspection surface (e.g., a photomask) through a thin pellicle or, alternatively, without any pellicle at all. As explained above, this depicted embodiment includes a first group of optical elements 202 which remains constant regardless of the type of pellicle used (e.g., thick, thin, or none). The depicted embodiment also includes a reconfigurable second group of optical elements 203. As depicted in FIG. 2(a), the second group of optical elements 203 is in a first mode of operation enabling the inspection of an inspection surface through a thin pellicle (or alternatively, without any pellicle at all).

As stated above, the first group of optical elements 202 is configured to achieve a high NA, a relatively long working distance, aberration correction, and beam contraction. In the depicted embodiment, the first group of optical elements 202 includes eight (8) optical elements having sixteen optical surfaces. The first group of optical elements 202 is identified as ($L_1$, $L_2$, $L_3$, $L_4$, $L_5$, $L_6$, $L_7$, $L_8$), respectively. Also identified are the sixteen optical surfaces S0, S1, S2, S3, S4, S5, S6, S7, S8, S9, S10, S11, S12, S13, S14, and S15, respectively. For the implementation illustrated in FIGS. 2(a) and 2(b), the parameters for the optical elements are provided in Tables 1A, 2A, and 2B. The depicted implementation is provided as an example of the broader concepts encompassed by the principles of the invention. As is known to persons having ordinary skill in the art, the number and type of optical elements can be varied. Also, the positioning and optical parameters for the optical elements can be varied in accordance with the principles of the invention.

In the following Table 1A, some parameters for the optical elements $L_1$–$L_8$ and the sixteen surfaces S0–S15 for the first group of optical elements are presented in tabular format. Radius refers to the radius of curvature of the indicated surface. Silica refers to fused silica, such as is commonly available from many manufactures. In this table, the linear dimensions are given in millimeters (mm).

TABLE 1A

Optical Prescription for a
First Group of Optical Elements

| LENS | Surface | Radius | Thickness | Material | Diameter |
|---|---|---|---|---|---|
|  |  |  | 7.789903 | Air |  |
| $L_1$ | S0 | 29.127 | 11.042 | Silica | 40 |
|  | S1 | 17.72 |  |  |  |
| space |  |  | 0.3 | Air |  |
| $L_2$ | S2 | 55.042 | 9.76 | Silica | 52 |
|  | S3 | 30.376 |  |  |  |
| space |  |  | 0.03 | Air |  |
| $L_3$ | S4 | 200.05 | 9.31 | Silica | 62 |
|  | S5 | 52.136 |  |  |  |
| space |  |  | 0.3 | Air |  |
| $L_4$ | S6 | −136 | 9.54 | Silica | 65 |
|  | S7 | 136 |  |  |  |
| space |  |  | 0.3 | Air |  |
| $L_5$ | S8 | −57.511 | 9.47 | Silica | 62 |
|  | S9 | −351.258 |  |  |  |
| space |  |  | 0.3022 | Air |  |
| $L_6$ | S10 | −33.97 | 9.35 | Silica | 53 |
|  | S11 | −66.47 |  |  |  |
| space |  |  | 1.039546 | Air |  |
| $L_7$ | S12 | −23.86 | 8.22 | Silica | 41 |
|  | S13 | −14.92 |  |  |  |
| space |  |  | 13.735133 | Air |  |
| $L_8$ | S14 | 27.978 | 4.43 | Silica | 27 |
|  | S15 | 77.793 |  |  |  |

NA = 0.857
EFL = 8.00 mm
Reference wavelength = 257.25 nm

As discussed above, the second group of optical elements functions as a reconfigurable optical aberration compensator. FIG. 2(a) illustrates the second group of optical elements 203 operating in a first mode optimized to image inspection surfaces through a thin pellicle or in the absence of a pellicle. The depicted second group of optical elements 203 includes three (3) optical elements having six optical surfaces. These optical elements 203 are identified as $L_9$, $L_{10}$, and $L_{11}$, respectively. Also identified are the six optical surfaces S16, S17, S18, S19, S20, and S21, respectively.

Tables 2A and 2B provide example parameters for the second group of optical elements 203 (optimized for inspection through a thin pellicle or in the absence of a pellicle) as illustrated in FIG. 2(a). Parameters for the optical elements $L_9$–$L_{11}$ and $L_{12}$–$L_{14}$ and the associated twelve surfaces S16–S27 for the second group of optical elements are presented in tabular format. Radius refers to the radius of curvature of the indicated surface. Silica refers to fused silica, such as is commonly available from many manufactures. In this table, the linear dimensions are given in millimeters (mm).

TABLE 2A

Optical Parameters for a
Second Group of Optical Elements Operating
in a First Mode Used to Image Through a Thin Pellicle

| LENS | Surface | Radius | Thickness | Material | Diameter |
|---|---|---|---|---|---|
|  |  |  | 6.25 | Air |  |
| $L_9$ | S16 | −15.268 | 3.53 | Silica | 20 |
|  | S17 | −10.249 |  |  |  |
| space |  |  | 12.8329 | Air |  |
| $L_{10}$ | S18 | 10.987 | 3.5 | Silica | 16 |
|  | S19 | 41.86 |  |  |  |

TABLE 2A-continued

Optical Parameters for a
Second Group of Optical Elements Operating
in a First Mode Used to Image Through a Thin Pellicle

| LENS | Surface | Radius | Thickness | Material | Diameter |
|---|---|---|---|---|---|
| space |  |  | 38.004 | Air |  |
| $L_{11}$ | S20 | 29.289 | 3.65 | Silica | 21 |
|  | S21 | 24.539 |  |  |  |

FIG. 2(b) illustrates another embodiment where the reconfigurable second group of optical elements is switched to a second mode of operation optimized for inspection through a thick pellicle 205. In the depicted embodiment, the second group of optical elements 203' in a second mode of operation, induces an optical aberration that enables the objective lens system to image the inspection surface through a thick pellicle. This depicted second group of optical elements 203' also includes three (3) different optical elements having six different optical surfaces. The optical elements of 203' are identified as $L_{12}$, $L_{13}$, and $L_{14}$, respectively. Also identified are the six associated optical surfaces S22, S23, S24, S25, S26, and S27, respectively.

TABLE 2B

Optical Parameters for a
Second Group of Optical Elements Operating
in a Second Mode Used to Image Through a Thick Pellicle

| LENS | Surface | Radius | Thickness | Material | Diameter |
|---|---|---|---|---|---|
|  |  |  | 2.3593 | Air |  |
| $L_{12}$ | S22 | −21.664 | 3.565 | Silica | 22 |
|  | S23 | −12.082 |  |  |  |
| space |  |  | 16.3505 | Air |  |
| $L_{13}$ | S24 | 12.114 | 3.86 | Silica | 16 |
|  | S25 | 52.266 |  |  |  |
| space |  |  | 37.9959 | Air |  |
| $L_{14}$ | S26 | 35.245 | 3.46 | Silica | 21 |
|  | S27 | 27.975 |  |  |  |

Thus, the back end of the lens system 201 can be reconfigured to support inspection machines that need to support both thick pellicle photomasks and thin pellicle (or no pellicle) photomasks. As previously described, the three elements (for the specific examples shown above) of the second group of optical elements (for both modes of operation) can be mounted in a separate cell (for example), and shuttled in/out in an automated fashion, depending on the type of photomask inspected. No aspheric surfaces are required in the designs described herein above.

However, the inventors contemplate that embodiments implementing aspherical optical elements can be used. For example, aspherical optical elements can be implemented to reduce the number of optical elements required in the second group of optical elements. Moreover, if the use of aspherical optical elements is combined with adjustments in pupil plane position and adjustments to the overall length of the design, then even fewer elements need to be changed in order to accommodate an objective lens system that can image through both thick and thin pellicles. However, such design parameters are traded off against other optomechanical system constraints as well as cost and manufacturability considerations.

Figure 3B:
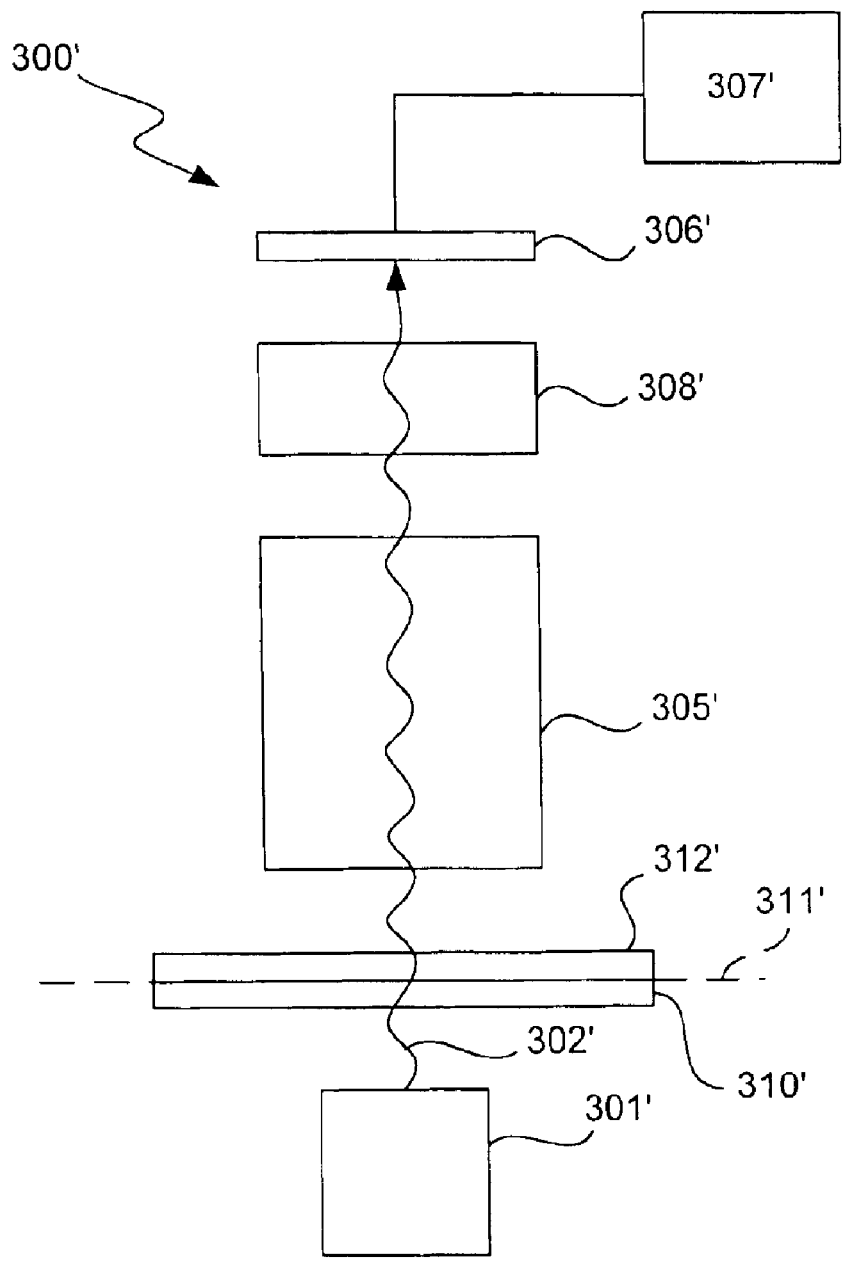

FIGS. 3(a), 3(b), and 4 are simplified schematic depictions of typical embodiments for optical inspection tools and objective lens systems constructed in accordance with the principles of the invention. Referring to FIG. 3(a), inspection tool 300 is constructed such that it can be used to inspect through thick pellicles, thin pellicles, or in the absence of any pellicle at all. To the inventor's knowledge, no inspection tool currently known has the flexibility to inspect through this range of pellicles using the same inspection tool. Such tools include a light source 301 that produces a light beam 302 suitable for illumination of an object 310 (e.g., a photo mask) such that the object 310 can be inspected. Many different types of light sources known to one having ordinary skill in the art can be used with the depicted embodiment. In one preferred implementation, the light source 301 is a 257.25 nm wavelength laser.

The light beam 302 is directed through the pellicle 312 (if one is present) and onto the inspection surface 310. In this depiction, the light beam 302 is directed onto a beam splitter 303 that directs a portion of the light beam 302 through an optical system 305 (such a system can include an objective lens system, as well as other optical elements and systems) onto the inspection surface 310. The optical system 305 focuses the light beam 302 at an object plane 311 where the inspection surface 310 is typically positioned. The optical system 305 is constructed such that it can achieve a high numerical aperture and a long working distance. Moreover, the optical system 305 is configurable such that, in different modes of operation, it enables the inspection of an inspection surface 310 in the absence of a pellicle, through a thin membrane pellicle, or through a thick pellicle. Light reflected by the inspection surface 310 passes back through the optical system 305 and possibly other optical elements (e.g., such as a depicted magnification element 308 or other optical elements) where it is detected (imaged) by a detector element 306. Such detector elements 306 can encompass a wide range of light detector elements known to persons of ordinary skill in the art. Such elements include a myriad of photodetector elements known to persons of ordinary skill in the art. Such elements can include, without limitation, photomultiplier tubes, photodiodes, CCD's, and arrays of such structures. Also, TDI (time domain integration) sensor arrays may also be used. Information obtained by such detector elements 306 is typically converted to electrical (or in some cases optical) signals that are transmitted to an image processor 307. The image processor 307 can conduct a wide range of operations on signals received from the detector element 306. Such, operations include, but are not limited to, data processing and signal and data analysis as well as a myriad of other operations known to persons having ordinary skill in the art. The image processor 307 can include, without limitation, microprocessors, computers, DSP's, ASIC's, memory, and a variety of other related electronic elements. Commonly, such image processors 307 include signal processing elements and/or modules that can conduct analysis of the detected images of the surface to detect, locate, and quantify defects.

It is to be specifically pointed out that the optical system 305 can be comprised of many optical elements. Although not limited to such, the optical system 305 can employ magnification systems, objective lens systems, as well as other optical systems commonly used by those having ordinary skill in the art. In particular, the optical system 305 can employ all of the optical systems disclosed in this patent. The optical system 305 also includes an objective lens system, which specifically includes, without limitation, all the objective lens systems described in this patent. Such systems are designed to permit the optical inspection tool 300 described herein to inspect inspection surfaces through thick pellicles, thin pellicles, or in the absence of any pellicle at all.

FIG. 3(b) is a simplified depiction of another related embodiment for an inspection system in accordance with the principles of the invention. The inspection tool 300' includes a light source 301' which produces a light beam 302' that is directed onto inspection surface 310' (e.g., a photo mask). Previously discussed light sources can be used. Also, the light source 301' can incorporate other optical elements such as relay optics, magnification optics, and objective lens systems, as well as other optical systems commonly used by those having ordinary skill in the art. The light beam 302' is directed onto the object (e.g., a photomask) 310' which is typically positioned in the object plane 311'. A portion of light beam 302' passes through the object 311' and through an optical system 305' (such a system can include an objective lens system, as well as other optical elements and systems). Light transmitted through the object 310' can pass through a thin or thick pellicle (schematically depicted by 312') where it is received and focused by optical system 305'. As before, optical system 305' (schematically depicted in FIG. 4) is constructed to operate in multiple modes while achieving high numerical aperture, aberration correction, and a long working distance. Importantly, the multiple modes of the optical system 305' enable the inspection tool 300' to inspect objects through thick pellicles, thin pellicles, or in the absence of pellicles altogether. To the inventor's knowledge, no photomask inspection tool currently known or in use has this inspection flexibility. Light 302' passes through optical system 305', through magnification element 308' (and optionally other optical elements) where it is detected by a detector element 306'. As before, detector elements 306' can encompass a wide range of light detector elements known to persons of ordinary skill in the art. An image processor 307' receives signal from the detector 306' and typically conducts analysis of an inspected object to detect, locate, and quantify defects. It is understood that the systems shown separately in FIGS. 3(a), and 3(b), may be combined into a single system, which can illuminate and image the photomask in either a reflective or transmissive mode.

The inventors also point out that the principles of the invention are not limited to the specific examples depicted in FIGS. 3(a) and 3(b). The objective lens embodiments of the present invention can be practiced with inspection tools that vary from those depicted in the referenced illustrations.

FIG. 4 is a simplified schematic depiction of one suitable embodiment of an objective lens system that can be included in an optical system (e.g., 305, 305') constructed in accordance with the principles of the invention. Such systems can form part of the optical inspection tools illustrated in, for example, FIG. 3(a) or 3(b). The implementation schematically depicted in FIG. 4 can include a first group of optical elements 202 and a reconfigurable second group of optical elements 203 (or 203'). These elements are well-described hereinabove with respect to FIGS. 2(a) and 2(b). Moreover, the inventors contemplate other embodiments of such objective lens systems. Such embodiments include, but are not limited to those embodiments discussed hereinbelow.

The inventors also contemplate another approach for constructing an objective lens system in accordance with the principles of the invention. In one such embodiment, the objective lens system includes a first and second group of optical elements arranged longitudinally with respect to each other. In one configuration, an optical corrector plate is inserted into the optical path between the first and second groups of optical elements to enable the objective lens system to inspect objects when no pellicle (or a very thin pellicle) is present. The same objective lens system is configured such that when the optical corrector plate is removed the lens system can be used to inspect objects through a thick pellicle.

In a modified approach, the first and second groups of optical elements are configured so that when the optical corrector plate is inserted into the optical path between the first and second groups of optical elements, the objective lens system can be used to inspect objects through a thick pellicle. Moreover, when the optical corrector plate is removed the lens system can be used to inspect objects through a thin pellicle or in the absence of a pellicle.

Other embodiments, include implementations where the first and second groups of optical elements remain constant and a specially constructed corrector plate is shuttled in and out of place depending on whether a thick or thin pellicle is used. Such implementations involve adjusting the lens parameters and configurations. For example, the first and second group of optical elements can be altered to optimize the system for such an implementation. Also, a different corrector plate is constructed for each mode of operation. Using the teachings set forth in this patent, coupled with skill possessed by one of ordinary skill in the art, such embodiments can be constructed.

While acceptable optical performance can be achieved by embodiments using an interposable corrector plate alone, even higher optical performance can be achieved if we combine this plate with some axial movement of a single optical element (e.g., a lens) or with axial movement of a group of optical elements. By moving an optical element (or group of optical elements), the airspace (the distance between the various optical elements) can be adjusted to improve the overall optical performance of the objective lens system. This general principle can be illustrated with reference to the simplified schematic illustrations of FIGS. 5(a) and 5(b). Typically, such embodiments couple the interposition of the corrector plate with some movement of the optical element(s). Typically, this involves translating an optical element (or group of optical elements) along a longitudinal axis until the objective lens system obtains the desired optical properties.

Figure 5A:
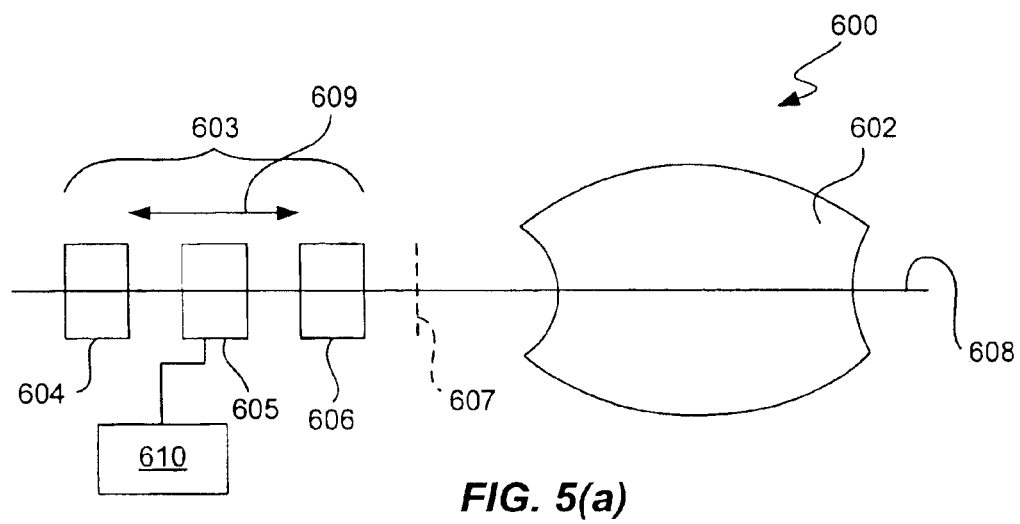
FIGS. 5(a) and 5(b) are schematic depictions of an embodiment of an objective lens system that incorporates an interposable corrector plate and an axial compensator in accordance with the principles of the invention.

FIG. 5(a) depicts an objective lens system 600 having a first group of optical elements 602 and a second group of optical elements 603. The second group of optical elements 603 can include a plurality of optical elements (or groups of optical elements)(604, 605, and 606) and an associated pupil plane 607 (indicated by the dashed line). The depicted lens configuration includes a longitudinal axis 608. Such an objective lens is intended to be suitable for inspection of photomasks. The configuration of FIG. 5(a) is suitable for inspecting an object through a thick pellicle. In order to inspect in the absence of a pellicle (or alternatively through a thin pellicle) the system is reconfigured. An optical element (or group of optical elements) 605 of the second group of optical elements 603 can be translated in a direction 609 (indicated by the arrow) along the longitudinal axis 608 until a suitable configuration is obtained. It is to be noted that all or some of the optical elements 604, 605, and 606 can be moved to achieve optimal performance. In the depicted embodiment, the optical element (or group of optical elements) 605 can be moved by using a suitable actuator 610. Additionally, a corrector plate (e.g., as discussed hereinabove) 611 can be inserted into the pupil plane 607 to achieve the desired optical properties for the system 600.

Figure 5B:
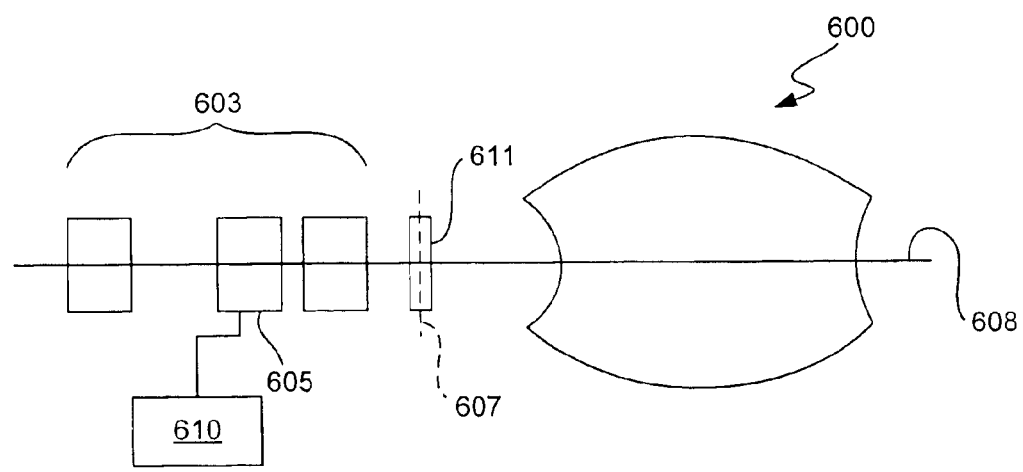

FIG. 5(b) schematically illustrates the change in configuration used by the depicted embodiment to inspect through a thin pellicle (or no pellicle). The optical element (or group of optical elements) 605 has been moved along the longitudinal axis 608 so that the second group of optical elements 603 obtains a desired configuration. Additionally, a corrector plate (e.g., as discussed hereinabove) 611 can be inserted into the pupil plane 607 to achieve the desired optical properties for the system 600.

The element(s) of the second group of optical elements 603 can be reconfigured by moving the affected optical elements (or groups of elements) using actuator elements 610. Suitable actuators 610 include, without limitation, piezo-electric actuators, electric motors, or a number of other opto-mechanical devices capable of accommodating precise lens movement in accordance with the principles of the invention. Repositioning an optical element, or group of optical elements, axially, as the imaging conditions are changed, is generically referred to herein, as axial compensation. The lens or groups of lenses that are axially translated (e.g., 605) are referred to as axial compensators.

In another implementation, a lens or a group of lenses can be arranged in a first configuration so that the objective lens system is optimized to image through a thin pellicle (or in the absence of a pellicle). Additionally, the lens or group of lenses can be reconfigured (typically by moving the subject optical elements along the longitudinal axis) into another configuration such that the objective lens system is optimized to inspect through a thick pellicle. Alternatively, as previously explained, a corrector plate can be introduced at a pupil plane to achieve further enhanced optical performance in conjunction with the adjustable airspace optical element(s). By introducing movable optical elements or movable groups of optical elements, the EFL and the magnification of the objective lens system can be altered. To compensate for this, zoom lenses of the magnification elements can be used to keep the overall system magnification relatively (within desired magnification parameters) constant. Thus, in these embodiments, an objective lens system incorporating movable optical elements (or groups of optical elements) can be used to achieve imaging through both thick pellicles and thin pellicles (or no pellicles at all). As stated, the aforementioned design can include an aspheric corrector plate which, when used in conjunction with the longitudinally movable lenses (i.e. the axial compensator), can be used to yield a high performance optical system for inspecting through both thick and thin pellicles.

Figure 6A:
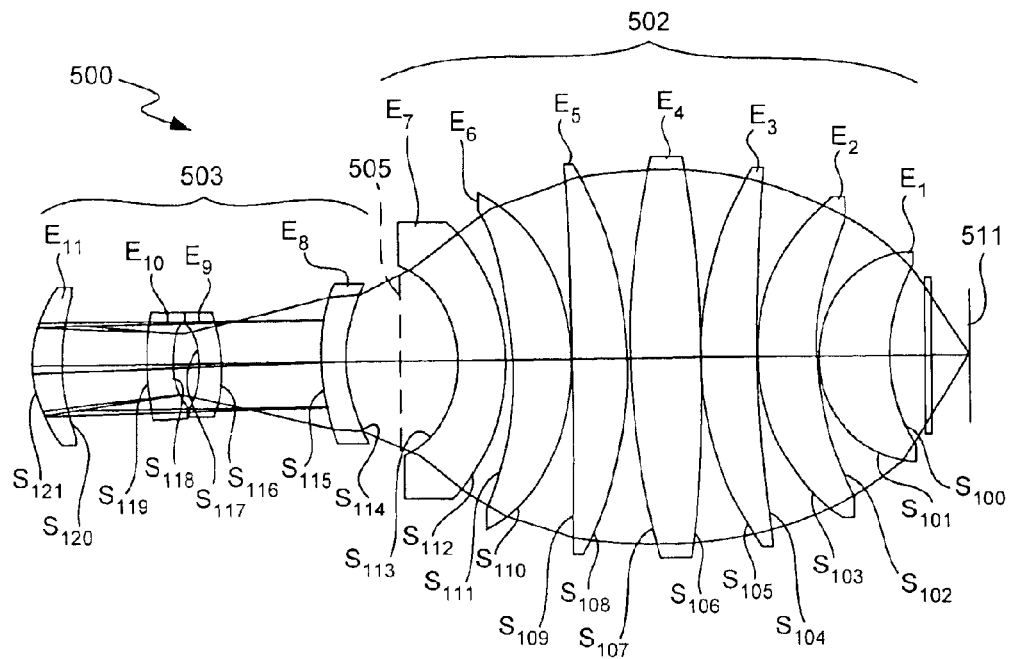
FIGS. 6(a) and 6(b) are schematic depictions of an embodiment of an objective lens system that incorporates an interposable corrector plate in accordance with the principles of the invention.
Figure 6B:
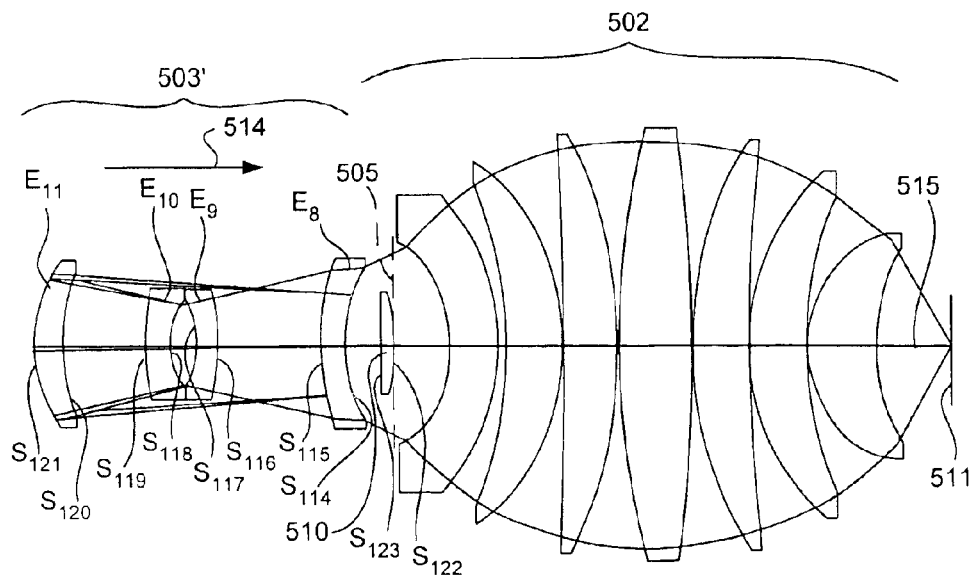

One specific embodiment of this more general principle is described as follows. FIGS. 6(a) and 6(b) depict yet one objective lens system embodiment constructed in accordance with the principles of the invention. This embodiment can be implemented as an objective lens system in a number of different inspection tools including, but not limited to, those depicted in FIGS. 3(a) and 3(b). Such an embodiment is similar to those discussed with respect to of FIGS. 2(a) and 2(b). As with the above-described implementations, the embodiments discussed below are capable of supporting two mode operation. In one mode (e.g., when a thick pellicle is present), objects are inspected using the first and second sets of optical elements. In another mode (e.g., when no pellicle or a thin pellicle is present) objects are inspected using the same first set of optical elements. However, the second set of optical elements is spatially reconfigured to optimize optical performance cooperatively with a corrector plate to achieve improved optical performance.

FIG. 6(a) depicts an objective lens system 500 having a first group of optical elements 502 at the finite conjugate side of the objective lens system 500. A second group of optical elements 503 is positioned at the infinite conjugate side of the objective lens 500. The first group of optical elements 502 can be configured to achieve a high numerical aperture, generate a relatively long working distance, and achieve beam contraction for light passing through the first group of optical elements 502. The second group of optical elements 503 includes a pupil plane 505 (indicated by the dashed line). The depicted lens configuration is suitable for inspection of photomasks. In particular, the depicted lens configuration is suitable for inspection of photomasks having a thick pellicle.

As stated, the embodiment depicted in FIG. 6(a) is optimized for inspection of objects through a thick pellicle. The spacing and prescription of each of the elements in the first group of optical elements 502 and the second group of optical elements 503 are optimized for imaging through a thick pellicle.

In contrast, the related embodiment of FIG. 6(b) is optimized for inspection of objects through a thin pellicle or objects having no pellicle. FIG. 6(b) depicts the interposition of an aspheric corrector plate 510 into the pupil plane 505 in accordance with the principles of the invention. Moreover, the second group of optical elements 503 is spatially reconfigured to form a reconfigured second group of optical elements 503'. The combination of reconfigured optical elements 503', optical elements 502, and corrector plate 510 serve to optimize the objective lens system for inspection in the absence of a pellicle (or with a thin pellicle). In the depicted embodiment, optical element $E_8$ is moved along the longitudinal axis 515 in direction 514 (as indicated by the arrow). The new position of optical element $E_8$ is such that when optically combined with the other elements ($E_9$, $E_{10}$, and $E_{11}$) of the reconfigured second group of optical elements 503', the first group of optical elements 502, and the corrector plate 510, the objective lens system 500 is capable of inspection of objects in the absence of a pellicle (or with a thin pellicle).

In other embodiments, other elements (or combinations of elements) of second group can be moved in order to appropriately reconfigure the second group of optical elements 503'. A number of different configurations and corrector plates can be implemented so long as the combination of reconfigured second group of optical elements 503', first group of optical elements 502, and corrector plate 510 serve together to optimize the objective lens system for inspection of objects in the absence of a pellicle (or with a thin pellicle). Alternatively, the initial configuration for the second group of optical elements 503 can be such that in the absence of the corrector plate 510 the objective lens system is capable of inspection of objects in the absence of a pellicle (or with a thin pellicle). In such a configuration, by spatially reconfiguring the second group of optical elements 503 and interposing the corrector plate 510 the objective lens system is capable of inspection of objects in through a thick pellicle.

In typical embodiments, the aspheric corrector plate 510 comprises a finite thickness optically polished glass slab, with one side being planar, and the other side having an aspheric surface profile. Alternatively, a thin binary optical element or holographic optical element may also be utilized in a similar fashion. In yet another embodiment, the binary optical element or holographic optical element, may be fabricated directly into the planar side (or even the aspheric side) of the corrector plate.

When it is necessary to conduct an inspection through a thin pellicle (or through no pellicle), the corrector plate 510 is moved into the pupil plane 505 and appropriate optical elements are moved to implement a reconfigured second group of optical elements 503'. The corrector plate 510 and reconfigured second group of optical elements 503' compensate for the optical aberrations induced when the thick pellicle 511 is removed from the system. When used with thick pellicles, the corrector plate 510 is shuttled out of position such that it does not interfere with the light beam and the reconfigured optical elements 503' are returned to their original spatial configuration. A single corrector plate 510 can be designed for use with multiple pixel sizes and multiple NA values. The aspheric corrector plate can be fabricated through standard optical polishing and machining methods.

In the following Tables 3A, 3B, 3C, and 3D, some example parameters for the optical elements of the embodiment depicted in FIGS. 6(a) and 6(b) are presented in tabular format. In these tables, the linear dimensions are given in millimeters. It is to be noted that these parameters apply to a specific example and are intended to be illustrative rather than limiting. It is noted that the invention is not restricted to the embodiments disclosed hereinabove and that the inventors contemplate many other implementations in accordance with the principles of the invention.

TABLE 3A

Optical Surface Prescription for a First Group of Optical Elements 502

| LENS | Surface | Radius | Thickness | Material | Clear Aperture |
|------|---------|--------|-----------|----------|----------------|
|      |         |        | 12.1533   | Air      |                |
| $E_1$ | S100   | 26.4229 | 11.4455  | Silica   | 28.01          |
|      | S101    | 16.9951 |          |          | 33.164         |
| space |        |        | 0.113     | Air      |                |
| $E_2$ | S102   | 50.3433 | 9.7482   | Silica   | 43.958         |
|      | S103    | 31.5841 |          |          | 48.226         |
| space |        |        | 0.1219    | Air      |                |
| $E_3$ | S104   | 212.795 | 9.1843   | Silica   | 55.25          |
|      | S105    | 53.8223 |          |          | 56.914         |
| space |        |        | 0.1       | Air      |                |
| $E_4$ | S106   | -195.68 | 12.5     | Silica   | 59.89          |
|      | S107    | 113.957 |          |          | 60.382         |
| space |        |        | 0.5548    | Air      |                |
| $E_5$ | S108   | -63.012 | 9.0003   | Silica   | 58.52          |
|      | S109    | -613.65 |          |          | 57.426         |
| space |        |        | 0.158     | Air      |                |
| $E_6$ | S110   | -31.539 | 9.9831   | Silica   | 49.976         |
|      | S111    | -58.83  |          |          | 46.988         |
| space |        |        | 1.1445    | Air      |                |
| $E_7$ | S112   | -29.687 | 7.9653   | Silica   | 41.066         |
|      | S113    | -16.211 |          |          | 28.61          |

TABLE 3B

Prescription for a Second Group of Optical Elements 503 (for use with a thick pellicle)(i.e., when no corrector plate is used)

| LENS | Surface | Radius | Thickness | Material | Diameter |
|------|---------|--------|-----------|----------|----------|
|      |         |        | 19.4643   | Air      |          |
| $E_8$ | S114   | 21.9436 | 4        | Silica   | 22.85    |
|      | S115    | 37.2996 |          |          | 22.65    |
|      |         |        | 16.683    | Air      |          |
| $E_9$ | S116   | -28.479 | 3.5      | Silica   | 14.698   |
|      | S117    | -12.252 |          |          | 12.784   |
|      |         |        | 4.6593    | Air      |          |
| $E_{10}$ | S118 | 10.429 | 4         |          | 12.732   |
|      | S119    | 40.4106 |          | Silica   | 15.138   |
|      |         |        | 13.3537   | Air      |          |

TABLE 3B-continued

Prescription for a Second Group of Optical Elements 503
(for use with a thick pellicle)(i.e., when no corrector plate is used)

| LENS | Surface | Radius | Thickness | Material | Diameter |
|------|---------|--------|-----------|----------|----------|
| $E_{11}$ | S120 | 30.4026 | 4.7809 | Silica | 20.9 |
|  | S121 | 19.3322 |  |  | 22.57 |

NA = 0.857
EFL = 8.00 mm
Reference wavelength = 257.25 nm

TABLE 3C

Prescription for a Reconfigured Second Group of Optical
Elements 503'
(for use with no pellicle or thin pellicle)

| LENS | Surface | Radius | Thickness | Material | Diameter |
|------|---------|--------|-----------|----------|----------|
|  |  |  | 18.7881 | Air |  |
| $E_8$ | S131 | 21.9436 | 4 | Silica | 22.85 |
|  | S132 | 37.2996 |  |  | 22.65 |
|  |  |  | 17.3592 | Air |  |
| $E_9$ | S133 | −28.479 | 3.5 | Silica | 14.698 |
|  | S134 | −12.252 |  |  | 12.784 |
|  |  |  | 4.6593 | Air |  |
| $E_{10}$ | S135 | 10.429 | 4 | Silica | 12.732 |
|  | S136 | 40.4106 |  |  | 15.138 |
|  |  |  | 13.3537 | Air |  |
| $E_{11}$ | S137 | 30.4026 | 4.7809 | Silica | 20.9 |
|  | S138 | 19.3322 |  |  | 22.57 |

NA = 0.857
EFL = 8.00 mm
Reference wavelength = 257.25 nm

TABLE 3D

Aspheric Surface Parameters for the Corrector Plate 510

| Surface | Radius | K | AD | AE | AF | AG |
|---------|--------|---|-----|-----|-----|-----|
| S122 | −74.3259 | 0 | −.145-e-4 | −.132-e-6 | .313-e-9 | −.112-e-10 |
| S123 | infinity | 0 | 0 | 0 | 0 | 0 |

The surface S122 of the corrector plate 510 faces toward the image plane, and the surface S123 is disposed facing the reconfigured second group of optical elements 503'.

The surface S122 is aspheric and can be described by the following equation:

$$X = \frac{CY^2}{1 + (1 - (K+1)C^2)^{0.5}} + ADY^4 + AEY^6 + AFY^8 + AGY^{10} + \ldots$$

where

X is the distance along the optical axis;

Y is the height from the optical axis;

C is the reciprocal of the vertex radius of curvature of the curved objective lens assembly surface;

K is the conic coefficient;

AD through AG . . . are aspheric coefficients of the $4^{th}$, $6^{th}$, $8^{th}$, and $10^{th}$, order. The value of the aspheric coefficients for the aspheric surfaces S122 and S123 are provided in Table 3B.

Such aspheric corrector plates can be fabricated through standard optical polishing and machining methods. Additionally, magneto-resistive polishing, focused ion-beam etching, or high-speed synchro-speed automatic polishing can be used. Binary optic and holographic phase plates can also be used. Such plates are typically formed microlithographically using techniques familiar to the microelectronics industry. Patterns are etched into fused silica plates through a series of mask and etch steps, to give a precise phase distribution as a function of radial position along the corrector plate.

The corrector plate 510 functions as part of a switchable (or interposable) optical aberration compensator. In FIG. 6(a) the corrector plate 510 is not optically engaged (i.e., operating in a second mode) optimized for inspection through a thick pellicle. In the implementation shown in FIG. 6(b) the corrector plate 510 and reconfigured second group of optical elements 503' operate together as the aberration compensator. As depicted, lens system is operating in a first mode (optically engaged) optimized for inspection through a thin pellicle or no pellicle.

The inventors point out that in some alternative embodiments, a corrector plate can be used with an interchangeable second group of optical elements. In such embodiments, the second group of optical elements can be alternated between modes as is done in the embodiments described with respect to FIGS. 2(a) and 2(b). In a first mode the corrector plate is not engaged whereas in the second mode the corrector plate is optically engaged. In alternative modes, such an embodiment can be used to inspect through a thick pellicle or alternatively through a thin pellicle (or no pellicle). Such implementations are merely a matter of adjusting the lens parameters and configurations. For example, the first and second group of optical elements can be altered to optimize the system for such an implementation. Also, the corrector plate is typically adjusted to accommodate the differing optical elements and operation needs of the system. Using the teachings set forth in this patent, coupled with skill possessed by one of ordinary skill in the art, such embodiments can be constructed.

The present invention has been particularly shown and described with respect to certain preferred embodiments and specific features thereof. However, it should be noted that the above-described embodiments are intended to describe the principles of the invention, not limit its scope. Therefore, as is readily apparent to those of ordinary skill in the art, various changes and modifications in form and detail may be made without departing from the spirit and scope of the invention as set forth in the appended claims. In particular, the inventors contemplate that embodiments of the invention can be used to construct inspection systems and objective lens systems capable of imaging inspection surfaces through both thick and thin pellicles using a variety of optical element configurations not specifically disclosed herein. Other embodiments and variations to the depicted embodiments will be apparent to those skilled in the art and may be made without departing from the spirit and scope of the invention as defined in the following claims. Further, reference in the claims to an element in the singular is not intended to mean "one and only one" unless explicitly stated, but rather, "one or more".

We claim:

1. An objective lens system suitable for achieving a high numerical aperture and a long working distance and reconfigurable such that, in different configurations the system enables the inspection of an object through pellicles of different thicknesses as well as in the absence of a pellicle, the system comprising:

a first group of optical elements suitable for achieving a high numerical aperture and achieving beam contraction for light passing through the first group of optical elements;

a second group of optical elements that, when switched to a first mode, enables the lens system to inspect an object through a thin pellicle and to inspect the object in the absence of a pellicle, and when switched to a second mode enables the lens system to inspect an object through a thick pellicle wherein the second group of optical elements, when switched to the second mode, induces an optical aberration that compensates for optical aberrations caused by the thick pellicle, thereby enabling the objective lens system to image the object through the thick pellicle.

2. The objective lens system of claim 1 wherein the first group of optical elements and the second group of optical elements, in combination, are arranged so that the objective lens system has a numerical aperture equal to or greater than about 0.85.

3. The objective lens system of claim 1, wherein the thin pellicle comprises a pellicle less than about 2 micron thick and wherein the thick pellicle comprises a pellicle greater than about 300 micron thick.

4. The objective lens system of claim 1, wherein the thick pellicle comprises a pellicle about 800 micron thick.

5. An objective lens system suitable for achieving a high numerical aperture and a long working distance and reconfigurable such that, in different configurations the system enables the inspection of an object through pellicles of different thicknesses as well as in the absence of a pellicle, the system comprising:
   a first group of optical elements suitable for achieving a high numerical aperture and achieving beam contraction for light passing through the first group of optical elements;
   a second group of optical elements that enables the lens system to inspect an object through a thick pellicle; and
   a removable corrector plate which is inserted into an optical path of the lens system to enable an inspection of the object through a thin pellicle and in the absence of a pellicle.

6. An objective lens system suitable for achieving a high numerical aperture and a long working distance and reconfigurable such that, in different configurations the system enables the inspection of an object through pellicles of different thicknesses as well as in the absence of a pellicle, the system comprising:
   a first group of optical elements suitable for achieving a high numerical aperture and achieving beam contraction for light passing through the first group of optical elements;
   a second group of optical elements that enables the lens system to inspect an object through a thin pellicle or in the absence of a pellicle; and
   a removable corrector plate that is inserted into an optical path of the lens system to enable inspection of the object through a thick pellicle.

7. An objective lens system suitable for achieving a high numerical aperture and a long working distance and reconfigurable such that, in different configurations the system enables the inspection of an object through pellicles of different thicknesses as well as in the absence of a pellicle, wherein the lens system comprises:
   a group of optical elements arranged together along a longitudinal axis to achieve a high numerical aperture, beam contraction, and a long working distance for light passing through the group of optical elements in order that the light can be focused upon an object through a thick pellicle;
   a pupil arranged along the longitudinal axis having a pupil plane, the pupil being arranged so that the light passes through the pupil plane,
   an aspheric corrector plate for insertion into the pupil plane to change inspection mode when the object is inspected through a thin pellicle or in the absence of a pellicle so that when the corrector plate is inserted into the pupil plane optical aberrations caused by the removal of the thick pellicle are corrected for, thereby enabling inspection of the object with no pellicle or through a thin pellicle.

8. The objective lens system of claim 7 wherein the pupil plane is located within the group of optical elements.

9. The objective lens system of claim 7 wherein the pupil plane is located outside the group of optical elements.

10. The objective lens system of claim 7 wherein the aspheric corrector plate comprises a finite thickness polished asphere.

11. The objective lens system of claim 7 wherein the aspheric corrector plate comprises a binary optical element.

12. The objective lens system of claim 7 wherein the aspheric corrector plate comprises a holographic optical element.

13. The objective lens system of claim 7 wherein at least one of the optical elements in the group of optical elements is configured as a movable optical element that can be longitudinally translated along a longitudinal axis of the lens system into a first configuration and a second configuration, that
   when in the first configuration, the group of optical elements together with the aspheric corrector plate inserted into the pupil plane, corrects for optical aberrations, enabling the inspection of the object through a thin pellicle and in the absence of a pellicle; and
   when in the second configuration and when the aspheric corrector plate is removed from the pupil plane, enables the inspection of the object through a through the thick pellicle.

14. The objective lens system of claim 13 wherein a magnification element of the system corrects for any alterations of magnification caused by the movable optical element.

15. The objective lens system of claim 7 wherein at least one of the optical elements in the group of optical elements is configured as a movable optical element that can be longitudinally translated along a longitudinal axis of the lens system into a first configuration and a second configuration, that
   when in the first configuration, the group of optical elements together with the aspheric corrector plate inserted into the pupil plane, corrects for optical aberrations, enabling the inspection of the object through a thick pellicle; and
   when in the second configuration and when the aspheric corrector plate is removed from the pupil plane, enables the inspection of the object through a through a thin pellicle and in the absence of a pellicle.

16. The objective lens system of claim 15 wherein a magnification element of the system corrects for any alterations of magnification caused by the movable optical element.

17. An optical inspection tool, comprising:
   a source of light;
   an optical system for achieving desired magnification and focusing the light onto an object at an image plane and configurable such that in different modes of operation it enables the inspection of the object in the absence of a pellicle, through a thin pellicle, and through a thick pellicle the optical system including:

a first group of optical elements suitable for achieving a high numerical aperture and achieving beam contraction for light passing throuuh the first group of optical elements;

a second group of optical elements configured to inspect the through a thick pellicle;

an aspheric corrector plate that is interposable between the first group of optical elements and the second group of optical elements to enable the inspection of the object through a thin pellicle and in the absence of the pellicle;

a detector element for detecting light from the object and producing an associated electrical signal; and image processor circuitry for processing the electrical signal to analyze the object.

18. An optical inspection tool, comprising:

a source of light;

an optical system for achieving desired magnification and focusing the light onto an object at an image plane and configurable such that in different modes of operation it enables the inspection of the object in the absence of a pellicle, through a thin pellicle, and through a thick pellicle the optical system including:

a first group of optical elements suitable for achieving a high numerical aperture and achieving beam contraction for light passing through the first group of optical elements;

a second group of optical elements configured to so that the object can be inspected through a thin pellicle and in the absence of a pellicle;

an aspheric corrector plate that is interposable between the first group of optical elements and the second group of optical elements thereby enabling the inspection of the object through a thick pellicle;

a detector element for detecting light from the object and producing an associated electrical signal; and image processor circuitry for processing the electrical signal to analyze the object.

19. An optical inspection tool, comprising:

a source of light;

an optical system for achieving desired magnification and focusing the light onto an object at an image plane, the system including:

a group of optical elements arranged along a longitudinal axis to achieve a high numerical aperture, beam contraction, and a long working distance for light passing through the group of optical elements;

a pupil arranged along the longitudinal axis having a pupil plane, the pupil being arranged so that the light passes through the pupil plane, an aspheric corrector plate for insertion into the pupil plane when no pellicle is used and when a thin pellicle is used with the object such that when the corrector plate is inserted into the pupil plane, optical aberrations are corrected permitting proper focus and inspection of the object, and so that when the corrector plate is removed from the pupil plane, the object can be inspected through a thick pellicle;

a detector element for detecting light from the object and producing an associated electrical signal; and image processor circuitry for processing the electrical signal to analyze the object.

20. The optical inspection tool of claim 19 wherein the optical system is an inspection tool configured to inspect semiconductor photomasks and wherein the object is a semiconductor photomask.

21. The optical inspection tool of claim 19 wherein at least one of optical elements in the group of optical elements is configured as a movable optical element that can be longitudinally translated along the longitudinal axis into a first configuration and a second configuration, such that when in the first configuration, the group of optical elements together with the aspheric corrector plate inserted into the pupil plane, enables the inspection of the object through a thin membrane pellicle and in the absence of a pellicle;

when in the second configuration and when the aspheric corrector plate is removed from the pupil plane, enables the inspection of the inspection surface through a thick pellicle.

22. The optical inspection tool of claim 21 wherein the optical system includes a magnification element that is adjusted to maintain the desired magnification as the configuration of the movable optical element is altered from one configuration to another configuration.

23. The optical inspection tool of claim 19 wherein the group of optical elements includes a first group of optical elements and a second group of optical elements wherein the second group of optical elements includes two modes of operation, a first mode for inspection of the object through a thin pellicle and in the absence of a pellicle, and a second mode for inspection of the object through a thick pellicle, such that when the second group of optical elements operates in the first mode the aspheric corrector plate is inserted into the pupil plane enabling the inspection of the object through a thin membrane pellicle and in the absence of a pellicle; and when the second group of optical elements operates in the second mode the aspheric corrector plate is removed from the pupil plane enabling the inspection of the inspection surface through a thick pellicle.

24. An objective lens system including in combination, a first group of optical elements suitable for achieving a high numerical aperture and achieving beam contraction;

a second group of optical elements for compensating for the optical effects caused by one of: the presence of a thick pellicle, the presence of a thin pellicle, and the absence of a pellicle;

said combination of first and second group of optical elements comprising a means for, in a first mode, enabling the inspection of an object through the thin membrane pellicle and enabling the inspection of the object in the absence of a pellicle and, in a second mode, enabling the inspection of the object through the thick pellicle; and an interposable corrector plate that is optically engagable with second group of optical elements to alter the mode of operation for the lens system.

25. The lens system of claim 24 wherein the second group includes an interposable corrector plate that, when optically engaged with second group of optical elements in the first mode, enables the inspection of the object through a thin membrane pellicle and enabling the inspection of the object in the absence of a pellicle and wherein when the interposable corrector plate is not optically engaged with second group of optical elements, the system operates in the second mode enabling the inspection of the object through a thick pellicle.

26. The lens system of claim 24 wherein the second group includes an interposable corrector plate that, when optically engaged with second group of optical elements in the second mode, enables the inspection of the object through a thick membrane pellicle and wherein when the interposable corrector plate is not optically engaged with second group of optical elements, the system operates in the first mode enabling the inspection of the object through a thin pellicle and enabling the inspection of the object in the absence of a pellicle.

27. An objective lens system including in combination,
   a first group of optical elements suitable for achieving a high numerical aperture and achieving beam contraction;
   a second group of optical elements for compensating for the optical effects caused by one of: the presence of a thick pellicle, the presence of a thin pellicle, and the absence of a pellicle wherein the second group includes at least one movable element which can be translated along a longitudinal axis of the lens system such that when the at least one movable element is positioned at a first location the second group of optical elements operates in the first mode enabling the inspection of the object through a thin membrane pellicle and enabling the inspection of the object in the absence of a pellicle; and
   wherein when the at least one movable element is positioned at a second location the second group of optical elements operates in the second mode enabling the inspection of the object through a thick pellicle.

28. The lens system of claim 27 wherein the second group includes an interposable corrector plate that, when optically engaged with second group of optical elements in the first mode, further enables the inspection of the object through a thin membrane pellicle and in the absence of a pellicle and wherein when the interposable corrector plate is not optically engaged with second group of optical elements when the system is operating in the second mode thereby enabling the inspection of the object through a thick pellicle.

29. The lens system of claim 27 wherein the second group includes an interposable corrector plate that, when optically engaged with second group of optical elements in the second mode further enables the inspection of the object through a thick pellicle and wherein when the interposable corrector plate is not optically engaged with second group of optical elements when the system is operating in the first mode thereby enabling the inspection of the object through a thin membrane pellicle and in the absence of a pellicle.

* * * * *